United States Patent [19]

Brooker et al.

[11] 4,104,026

[45] Aug. 1, 1978

[54] IMMUNOASSAY SEPARATION TECHNIQUE

[75] Inventors: Gary Brooker; Wesley L. Terasaki; Michael G. Price, all of Charlottesville, Va.

[73] Assignee: University of Virginia, Charlottesville, Va.

[21] Appl. No.: 730,630

[22] Filed: Oct. 7, 1976

Related U.S. Application Data

[63] Continuation-in-part of Ser. No. 666,302, Mar. 12, 1976, Pat. No. 4,022,577.

[51] Int. Cl.$^2$ .................. G01N 33/16; G01N 23/12
[52] U.S. Cl. ..................... 23/230 B; 23/253 R; 424/1; 424/1.5; 424/12
[58] Field of Search ............. 23/253 R, 230 B, 259; 424/12, 1, 1.5; 195/127, 103.5 A

[56] References Cited

U.S. PATENT DOCUMENTS

| | | | |
|---|---|---|---|
| 3,690,833 | 9/1972 | Ferrari | 23/253 R |
| 3,843,326 | 10/1974 | Lichtenstenen | 23/253 R |
| 3,896,217 | 7/1975 | Johnson | 424/12 |
| 4,009,005 | 2/1977 | Johnson | 23/253 R |

*Primary Examiner*—R.E. Serwin
*Attorney, Agent, or Firm*—Oblon, Fisher, Spivak, McClelland & Maier

[57] ABSTRACT

In a method for effecting immunoassay of a multiplicity of samples, each possibly containing an antigen or an antibody to be assayed, wherein each sample is incubated with a solution containing a detectable antigen or antibody to form a multiplicity of mixtures, each mixture containing as components complexed antigen-antibody, non-complexed antigen and non-complexed antibody, separating at least one of the components of said mixture by adsorption and thereafter detecting the quantity of detectable antigen or antibody, in one of the non-adsorbed portions of the mixture, the improvement which comprises continuously and sequentially separating at least one component intended to be separated from each of said multiplicity of mixtures by passing a first mixture from said multiplicity of mixtures over an adsorbent which adsorbs the components intended to be separated from said mixture, removing from said adsorbent the non-adsorbed portion of said mixture, and repetitively passing each next succeeding mixture from said multiplicity of mixtures over the same adsorbent without intermittent removal of the components of the mixture which had been adsorbed onto said adsorbent from the preceding mixtures, and removing from said adsorbent the non-adsorbed portion following each pass, wherein each sequential mixture is in contact with said adsorbent for a residence time which is sufficient to permit adsorption of the said component, but which is insufficient to effect significant disassociation of the prior adsorbed component, and which is insufficient to effect adsorption of additional components of said mixture onto the additional adsorption sites created on said adsorbent by the prior adsorption of the components from the preceding mixture. Apparatus is also provided for effecting said method.

14 Claims, 15 Drawing Figures

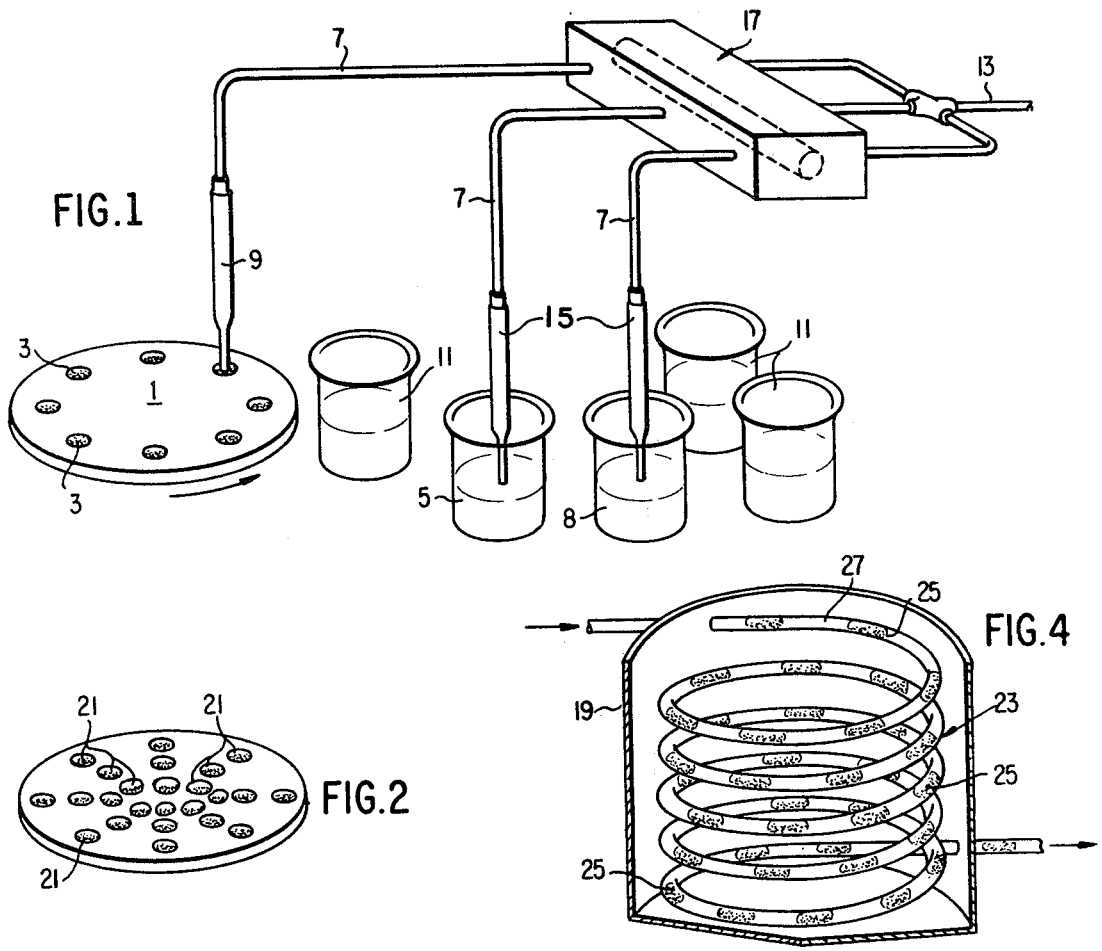
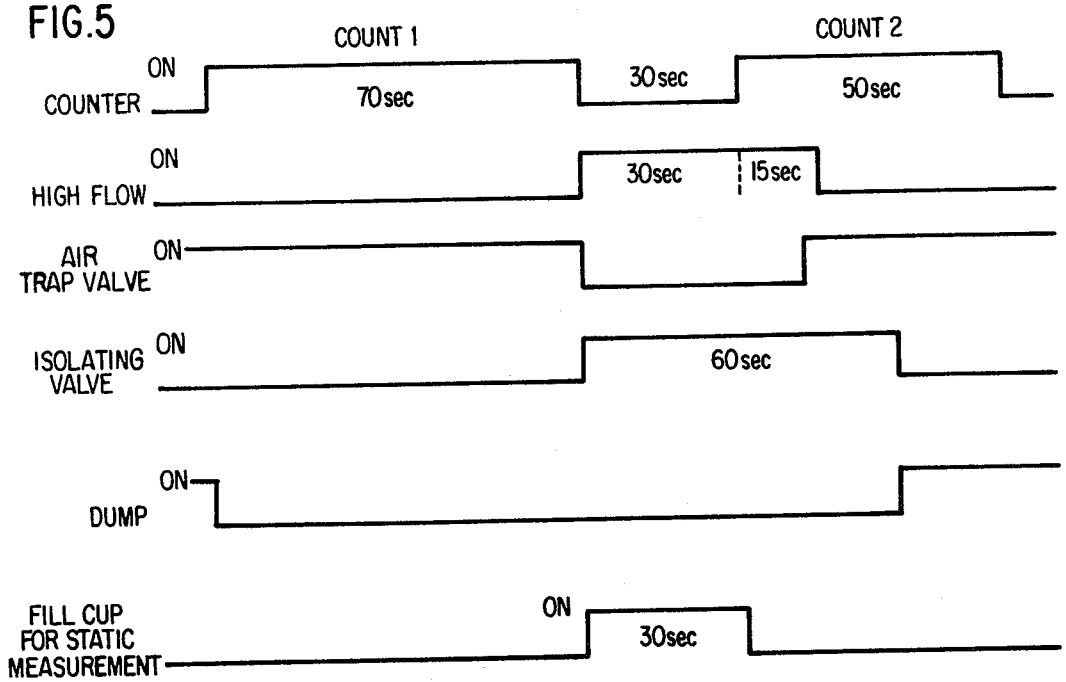

IMMUNOASSAY SEPARATION TECHNIQUE

CROSS-REFERENCE TO RELATED APPLICATION

This application is a continuation-in-part of application Ser. No. 666,302 filed Mar. 12, 1976, U.S. Pat. No. 4,022,577.

BACKGROUND OF THE INVENTION

1. Field of the Invention

The present invention relates to a method for separating antigenantibody complexes from solutions containing free antigens or antibodies. More particularly, the present invention relates to a technique wherein an adsorbent material is used to effect such separation for a multitude of samples without regeneration of the absorbent between samples. This technique is useful in automated immunoassay techniques.

2. Description of the Prior Art

Isotope displacement using specific antibodies to measure minute quantities of insulin was first reported by *Yalow et al* (Nature 184, 1648) which has led to the widespread practice of this technique for the analysis of a wide variety of biologically important substances. Radioimmunoassay has become a primary technique for the routine analysis of literally hundreds of biochemical and clinically important substances. Radioimmunoassay is now the method of choice for the analysis of many substances, because antibodies with very high selectivity and affinity can be produced which permit measurement of any desired compound in rather impure samples. The amount of impurity can, in many cases, be $10^9$ times that of the substance of interest and not interfere with the measurement. This extraordinary selectivity and ability to detect femtomole ($10^{-15}$ mole) quantities of substances has pushed the radioimmunoassay to the forefront of modern analytical chemistry.

If the radioimmunoassay has any limitations at all, it is the amount of manual labor and time required to obtain results. A typical assay first involves the combination of the unknown sample or standard, specific isotope tracer and antibody. This solution is then incubated in the cold or at room temperature for at least 20–30 minutes to as long as several days to obtain equilibrium between the antigen (ligand molecule being measured) and the antibody. The antibody bound ligand isotope is then separated from the solution. This is generally accomplished by addition of dextran coated charcoal to absorb the free ligand, by precipitation of the antibody-isotope complex with ammonium sulfate or ethanol or by some other technique such as molecular seive chromatography. The isotope antibody complex is recovered after centrifugation or collection of a specific column fraction and the radioactivity determined usually in an automatic beta or gamma counter. The amount of unknown substance present is determined from standard curves constructed from standards measured at the same time. Increasing additions of unknown sample reduces the specific activity of the isotope tracer thus yielding less radioactivity bound to the antibody.

The manual processing of samples for radioimmunoassay is time consuming, costly and requires meticulous attention to detail. In one laboratory alone, 8000 to 10,000 test tubes per month may be used for radioimmunoassay purposes. The repetitive nature and high precision of these determinations is responsible for considerable variability in the quality and reproducibility of the results. It is obvious that the complete automation of this technique would, of course, be desirable. Several attempts to automate radioimmunoassays have only met with limited success.

The major reason radioimmunoassays (or immunoassays) have not heretofore been readily adapted to automated analysis has been the difficulty in devising on-line methods to separate the antigen-antibody complex from the free antigen or antibody.

For instance, in Johnson, U.S. Pat. No. 3,896,217, a method is provided wherein a sample containing an unknown concentration of a specific antigen, and containing a known concentration of the same antigen tagged with a radioactive isotope, is passed through a bed of an immobilized antibody which is specific in its reactivity for the antigen being detected. As the solution is passed through the bed, both tagged and untagged antigen are bound to the immobilized antibody. It is essential that insufficient antibody is provided in the bed to react with all of the antigen in the solution; the solution passing through the antibody bed will contain both untagged and tagged antigen which is passed into a detector where the amount of unbound, tagged antigen present is measured. The bed must then be washed with a regenerating solvent which extracts all of the bound antigen, and the released antigen is passed into the detector for measurement of the quantity of tagged antigen which has been bound. The results are then correlated to a standard curve for determination of the concentration of untagged antigen in the original sample. This technique however, is not completely satisfactory, since it requires a substantial time delay to effect the necessary extraction of the antigen and regeneration of the immobilized antibody, and consequently, is not completely amenable to rapid analysis, which would be necessary to effect analysis of a multiplicity of samples. In the Johnson technique, it is necessary to use a sufficiently low concentration of immobilized antibody to bind only a portion of the antigen.

Another approach to automated radioimmunoassay has been described by Ertingshausen et al (Clinical Chemistry 21, 1305, 1975). The technique involves the initial automatic pipetting of antibody and antigen reagents followed by precisely timed incubation of the mixed ingredients. Each sample containing the antigen, antibody and the antigen-antibody complex are resolved into a fraction containing the antigen-antibody complex by passing the mixture through individual molecular seive columns, much the way that manual assays are currently performed. One column is thus used for each sample and usually discarded after the analysis. Radioimmunoassays of samples are determined in a static system similar to other conventional techniques, and the concentration of antigen in the original sample is determined by the use of preobtained, standardized curves. This procedure is burdened with much the same manual operational procedures as other prior art techniques which do not permit the continuous and rapid determination of a multiplicity of antigen containing samples.

Alternative approaches involve precipitation or filtration of a double antibody complex (E. Klin. Chem. Klin. Biochem. 13 Jg 1975, 481) or reacting the antigen in an antibody gel (Clin. Chem. 21, 829).

The weakness of all of these methods is that they require a separate separation column or material for each sample being processed. A need therefore has existed for a simple continuous technique to separate the antigen-antibody complex from free antigen or antibody in solution.

SUMMARY OF THE INVENTION

In a method for effecting immunoassay of a multiplicity of samples, each possibly containing an antigen or an antibody to be assayed, wherein each sample is incubated with a solution containing a detectable antigen or antibody to form a multiplicity of mixtures, each mixture containing as components complexed antigen-antibody, non-complexed antigen and non-complexed antibody, separating at least one of the components of said mixture by adsorption and thereafter detecting the quantity of detectable antigen or antibody, in one of the non-adsorbed portions of the mixture, the improvement which comprises continuously and sequentially separating at least one component intended to be separated from each of said multiplicity of mixtures by passing a first mixture from said multiplicity of mixtures over an adsorbent which adsorbs the components intended to be separated from said mixture, removing from said adsorbent the non-adsorbed portion of said mixture, and repetitively passing each next succeeding mixture from said multiplicity of mixtures over the same adsorbent without intermittent removal of the components of the mixture which has been adsorbed onto said adsorbent from the preceding mixtures, and removing from said adsorbent the non-adsorbed portion following each pass.

wherein each sequential mixture is in contact with said adsorbent for a residence time which is sufficient to permit adsorption of the said component, but which is insufficient to effect significant disassociation of the prior adsorbed component, and which is insufficient to effect adsorption of additional components of said mixture onto the additional adsorption sites created on said adsorbent by the prior adsorption of the components from the preceding mixture. Apparatus is also provided for effecting said method.

BRIEF DESCRIPTION OF THE DRAWINGS

FIG. 1 is a schematic of a preferred sampling system used in this invention;

FIG. 2 is a schematic of an alternate disc sampler for use in the system of FIG. 1;

FIG. 4 is a schematic diagram of a suitable incubation system used in the apparatus of FIG. 3;

FIG. 5 is a timing diagram to show the sequence of valves opening and closing as required by the apparatus of FIG. 3;

DETAILED DESCRIPTION OF THE PREFERRED EMBODIMENTS

Figure 3:
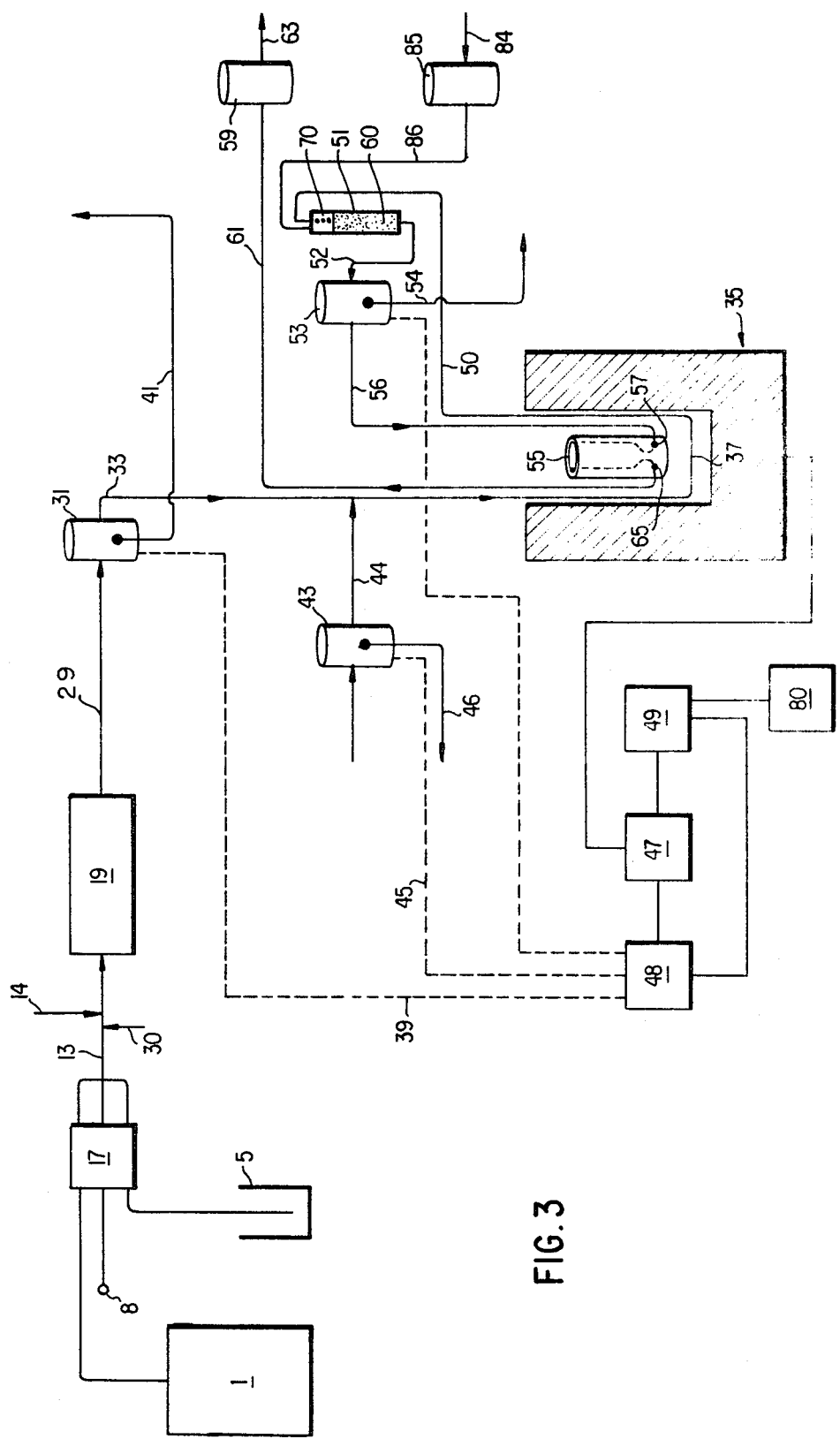
FIG. 3 is a schematic diagram of the apparatus of this invention.

According to the present embodiment of the invention, immunoassay of a multiplicity of samples is achieved. The sample which is suspected to contain an antigen, or an antibody to be assayed, is first mixed with a solution of a detectable antigen or antibody. The antigen or antibody can be made detectable by reacting a detectable ligand therewith, such as a radioactive isotope, a fluorescent compound, a luminescent compound, a bioluminescent compound, an enzyme, another antibody, or another antigen, by a variety of known techniques.

The mixture is incubated so that the detectable antigen or antibody is complexed with the antibody or antigen, if any, in the sample being assayed. It is possible, for instance, to use a detectable antigen to complex with possible antibodies in the sample. Alternatively, it is possible to use a detectable antibody to complex with possible antigens in the sample. Still alternatively, it is possible to mix and incubate an antibody solution and a solution of detectable antigen with the sample being assayed, which is suspected of containing antigen, so that the detectable antigen competes with any sample antigen for the available antibody.

A separation of one of the components of the incubated mixture is then effected and the remainder is measured for the presence of detectable antigen, or detectable antibody. The quantity perceived in the measurement is then a measure of the relative quantity of antigen or antibody contained in the sample.

This method of effecting an immunoassay is now conventional. It is not considered to be the critical aspect of the present invention. The present invention is concerned with a technique of separating one of the components of the incubated mixture from the other components. Thus, following the incubation of the sample with at least a solution containing the tagged antigen or tagged antibody, it is necessary to separate out the antigen-antibody complex formed, or to separate out the unreacted antibody, or the unreacted antigen. Alternatively, if the incubation is of a mixture of sample, detectable antigen solution, and a known quantity of antibody, then the separation might be of the combination of unreacted antibody and antigen-antibody complex. If the incubation is of a mixture of detectable antigen solution and a sample possibly containing an antibody, the incubated mixture will contain the antigen-antibody complex and unreacted antibody and unreacted antigen. One might separate out the antibody, and the antigen-antibody complex, or one might separate out the antigen and the antigen-antibody complex.

The separation of the desired component is conventionally carried out by adding an adsorbent to the components, or by precipitation or filtration techniques. The adsorbent might be specific for the antigen, or it might be specific for the antibody. A very wide range of adsorbent materials may be used for this purpose, as is well known in the art.

The difficulty in the prior art however, which has hindered the development of a truly automated continuous system, is that, heretofore, it was believed that following the separation of the component on the adsorbent, it thereafter becomes necessary to either dispose of the adsorbent, or it becomes necessary to regenerate, or to remove the adsorbed material from the absorbent before it is contacted with another incubated mixture to be separated. There existed quite plausible rationales for regenerating the adsorbent, or for disposing of the adsorbent without reuse. One rationale was based on the fact that once a component has become adsorbed onto the adsorbent, the nature of the adsorbent material shifts from one which is specific to the adsorption of the desired component to one which can also adsorb the undesired components. In other words, if the separation being effected is adsorption of antigen, the critical adsorbent material would be an adsorbent which is specific for the antigen in the system. After the antigen is adsorbed onto the adsorbent, the next sample will see an immobilized antigen. Since the antibody will readily complex with the antigen, the next sample coming into contact with the used adsorbent will see a large number of immobilized antigens as well as the adsorbent sites for the antigen. The expectation would thus be that a portion of the antibody in the next sample would be complexed by the immobilized antigen, which, of course, would make accurate assay determination impossible. With each succeeding sample, the situation would expect to get worse, if the adsorbent is not changed or regenerated. Thus, each succeeding sample would come into contact with the used adsorbent which contains the antigens or antibodies (as the case might be) of all of the preceding samples, which would be expected to increase the probability of adsorption of the wrong components, and even possibly result in the failure of the adsorbent to adsorb all of the desirable components. Thus, it would have been expected that each succeeding assay would result in a more indistinct separation and hence the assay results would become increasingly inaccurate.

Besides the danger that the next succeeding incubated mixture will suffer adsorption of the undesired component of the mixture due to the change in the nature of the adsorbent by adsorption of the preceeding sample, there is also the danger that the succeeding samples will elute the adsorbed material. Thus, if the adsorbed material is an antigen, the antibody content of the succeeding incubated mixtures could act to combine with the antigen already adsorbed onto the column, and instead of becoming complexed therewith as discussed above, it could cause removal of the antigen from the adsorbent to form additional complexed material.

Moreover, in some systems, such as in "solid phase" systems, disposal or regeneration of the adsorbent was the only possible way of carrying out the system.

The prior art therefore always at least regenerated the adsorbent, and usually disposed of the adsorbent between samples. Disposal of the adsorbent was not considered to be too great a difficulty since the cost of most adsorbents is modest and of little concern to the overall assay.

The difficulty this requirement led to, however, was far more serious than the mere cost of the adsorbent itself. Presently, the cost of carrying out a series of immuno assays is very high in terms of skilled personnel required, and in terms of time required. While it is long been recognized that it would be desirable to be able to automate the assay procedure to reduce these costs, each attempt lead to the same problem. Instead of attempting to meet the problem directly, prior attempts at automation tried to accomodate the need for regeneration or replacement of the adsorbent. The result of the attempt to accomodate the problem was to add significantly to the complexity and hence the cost of automated systems, or to increase the assay time per sample to the point that little, if any, time was saved over non-automated systems. For instance, in the Johnson U.S. Pat. No. 3,896,217, discussed at length above, there is used a system of regeneration of the adsorbent after each sample was passed therethrough. The result was a drastic increase in processing time, since complete regeneration of the adsorbent can be quite time consuming.

The present inventors have now discovered that the previous belief that the adsorbent must be disposed of, or regenerated, is not accurate, and in fact given the proper conditions, the adsorbent can be repetively reused, sample after sample, even up to 1000 samples in many cases. It is only critical that the residence time of the sample contacted with the adsorbent be sufficient to permit adsorption of the desired component, but insufficient to effect significant disassociation of the prior adsorbed component. Moreover, the residence time must be insufficient to permit adsorption of additional components of said mixture onto the additional sites created on the adsorbent by the prior adsorptions of the components from the preceeding mixtures.

Thus, it has been found that for incubated mixtures applied to the adsorbent of from 10 microliters to 10 ml size, which is brought into close contact with 100 microliters to 100 ml of adsorbent material, the residence contact time will be from 1 second to 120 seconds, and preferably from 10 seconds to 30 seconds.

The medium for effecting the contact is preferably a packed column containing particles of the adsorbent. The particles of adsorbent may be a size of from 10 − 1000 mesh. The adsorbent might alternatively be in a sponge form through which the solution is contacted, or it may be an adsorbent coated onto inert particles, or onto the walls of thin tubes. The adsorbent might also be contained in a slurry form, such as an aqueous slurry, and the mixture to be separated can be admixed in agitated condition with the slurry.

The temperature at the time of contact between the incubated mixture and the adsorbent may be from 0° C − 90° C, and preferably about ambient temperature. Of course, the higher the temperature, the shorter the contact time must be to minimize the antibody-antigen reaction. Also, the upper range of temperatures is not as desireable as the ambient temperature range, since the higher temperatures can have an undesirable effect on the stability of the antibody or antigen contained in the mixture.

Following the contact period between the incubated mixture and the adsorbent, the non-adsorbed material is removed from the contact station.

If the contact station is an adsorption column, the column may be washed out with a buffer solution. This is not intended to mean that the adsorbent material is being regenerated thereby. The purpose of the wash would merely be to pick up tailings from the previously treated mixture so as to prevent contamination of the succeeding sample. Of course, as is well known, regeneration of the column, which implies removal of the adsorbed material, requires a much longer time period than simple rinsing of the adsorbent to remove loosely adhering unadsorbed tailings from the previously treated mixtures.

The non-adsorbed components of the mixture are then brought to a measuring station for subsequent quantitative determination of the detectable antigen or antibody, as in now conventional systems.

The adsorbent is thereafter ready to receive the next sequential incubated mixture for component adsorption. Since the time period for the adsorption is, as indicated above, necessarily quite short, a very large number of incubated mixtures can be treated in quick succession. As one sample which has alrealy been subjected to adsorption is being subjected to the final measurement, the next sample may already be fed into the separation means for adsorption in preparation for the final measurement. Thus the present system can be operated in an extremely rapid, efficient, and continuous manner, which is entirely unlike any existing automated immuno assay system.

A wide variety of antigens and antibodies and complexes of the same can be treated by the methods of this invention. For instance, suitable antigens and their corresponding antibodies and complexes which can be separated, include:

Pituitary hormones
  Growth hormone
  Adrenocorticotropic hormone (ACTH)
  Melanocyte-stimulating hormone (MSH)
    α-MSH
    β-MSH
  Glycoproteins
    Thyroid-stimulating hormone (TSH)
    Follicle-stimulating hormone (FSH)
    Luteinizing hormone (LH)
  Prolactin
  Lipotropin (LPH)
  Vasopressin
  Oxytocin
Chorionic hormones
  Human chorionic gonadotropin (HCG)
  Human chorionic somatomammotropin (HCS)
Pancreatic hormones
  Insulin
  Proinsulin
  C-peptide
  Glucagon
Steroids
  Aldosterone
  Testosterone
  Dihydrotestosterone
  Estradiol
  Estrone
  Estriol
  2-Hydroxyestrone
Prostaglandins
Thyroidal hormones
  Triiodothyronine
  Thyroxine
Drugs
  Digoxin
    Digitoxin
  Morphine
  LSD
Cyclic nucleotides
  cAMP
  cGMP
  cIMP
  cUMP Calcitropic hormones
  Parathryoid hormone (PTH)
  Calcitonin (CT)
Gastroinestinal hormones
  Gastrin
  Secretin
  Cholecystokinin-pancreozymin (CCK-PZ)
  Enteroglucagon
Vasoactive tissue hormones
  Angiotensins
  Bradykinins
Hypothalamic-releasing factors
  Thryotropin-releasing factor (TRF)

Enzymes
  $C_1$-esterase
  Fructose 1,6-diphosphatase
Virus
  Australia antigen (HAA)
Tumor antigens
  Carcinoembryonic antigen
  α-Fetoprotein
Serum proteins
  Thyroxine-binding globulin
  Immunoglobulin G (IgG)
  Albumin
Other
  Intrinsic factor
  Rheumatoid factor
  Folic acid
  Neurophysin Suitable adsorbents which can be used in accordance with this invention include:

NONSPECIFIC MATERIALS USABLE FOR ANTIGEN-ANTIBODY SEPARATIONS

| Material | Mode of Binding | Examples of Commercially Available Material which can be used |
|---|---|---|
| Styrene divinylbenzene Polystyrene Epoxyamine Polyalkyleneamine Acrylic Polymer Cellulose Dextran Polymer | Ion Exchange | Aminex   Amerlite Dowex Bio-Rad AG   Dualite Bio-Rex Chelex   Permitite CM-Cellulose DEAE-Cellulose |
| Agarose Glass and Silica | | DEAE-Sephadex QAE-Sephadex DEAE-Biogel CM-Biogel |
| Hydroxyapatite Cellulose Silica Gel Alumina Polystyrene Charcoal | Absorption | Biogel HT Dowex Cellex N Bio-Sil A |

The oft used term "adsorbent" is used in the present application in its broadest sense to mean a material which binds with the antigens or antibodies by absorption, adsorption, or binding by relatively stable association of two substances irrespective of the actual chemical nature of the association.

In the following description, the reference numerals refer to the numerals in the several Figures, as briefly described above.

As disclosed in the said parent application, radioimmunoassay is carried out continuously and automatically, including reagent addition, separation of bound ligand from the total incubation mixture and radioactivity determination on line without any human intervention. The first results become available within 3-30 minutes, and in some instances, faster, and a new sample is thereafter processed every one and one-half to three minutes. One system according to the present invention can process over 400 samples per day, a rate which would be difficult to achieve by several technicians using presently available conventional automatic radiation counters.

For simplicity the system will be described for the case wherein an unknown antigen is measured using a tagged antigen and an antibody of known titer. It would be, of course, a simple matter to measure an unknown amount of antibody using the same tagged antigen. Alternatively, an unknown amount of antigen may be determined by using a tagged antibody. In all of these cases the process is essentially the same: after the antigen-antibody interaction has occurred, the antigen-antibody complexes are separated from the non-complexed forms.

In this illustration, the antigen sample is mixed with a solution of an antigen which has been reacted with or "tagged" with a radioactive isotope, and with a solution of an antibody. The antigen sample may be one which has been obtained from such biological sources as blood, sera, plasma, ascites or the like, which is suspected of containing specific antigens. The antibody solution is obtained from known, commercil sources, and is selected specific to the specific antigen or antigens intended to be detected. The titer of the antibody in the antiserum is known, and also the concentration of the antigen tagged with the isotope is known. The dilution of the antibody solution is selected so that insufficient antibody is present to react with the total quantity of antigen expected to be present in the system. The antibody can be used in this system in a very high dilution, as high as 1/200,000. it is somewhat surprising that the antibody remains sufficiently stable for the purposes of this system.

Isotopic tagging of the antigen can be effected by conventional techniques such as by reacting the antigen with moieties that will leave residual amount of $^{125}I$ or $^{131}I$, or any other suitable radioactive isotope as is known in the art such as $^{75}Se$, $^{3}H$, $^{14}C$, or 32p. Alternatively nonradioactive "tags" may be used provided that there are suitable detection means. Examples are luminescent, bioluminescent, ultraviolet, visible and infrared adsorbing compounds, etc.

The concentration of the tagged antigen solution can vary from one millimole to the limits of concentrations of isotope detectable by the radioactivity detection, usually one femtomole. The dilution of the antisera in the antibody solution can be from 1:10 to 1:500,000, depending upon the characteristics of each respective antiserum. Instead of a single antibody or a single antigen, two or a plurality of different tagged antigens and different antibodies can be used in combination to give a simultaneous multiple assay. Representative of the tagged antigen systems which might be used include: $^{125}I$-Digoxin, $^{131}I$-Thyroxine, $^{125}I$-secretin, $^{32}P$-cyclic AMP, $^{131}I$-Insulin, $^{125}I$-Glucagon, $^{75}Se$-Cortisol, $^{125}I$-Angiotensin I, $^{125}I$-Carcinoembryonic antigen, $^{125}I$-Somatostatin, $^{131}I$-Insulin, $^{131}I$-Triiodothyronine, $^{125}I$-Thyroxine, $^{125}I$-Growth Hormone, $^{125}I$-cyclic AMP, $^{131}I$-cyclic GMP, $^{125}I$-Morphine, $^{125}I$-Vasopressin, $^{131}I$-Aldosterone derivative and their respective antibodies. The antigens and antibodies could be contained in sera, urine or other buffers commonly used in the presently known art of radioimmunoassay such as sodium acetate, Tris-HCl, Barbital, Phosphate, MES, TES, etc. The sample being assayed could be measured at several dilutions such as 1:1, 1:2, 1:5, 1:10, 1:100, 1:1000, etc.

The two solutions and the sample being assayed are stored in separate containers until ready for mixing. One especially good sampling system is a disc sampler as shown in FIG. 1. In this system, a rotatable disc 1 holds a multiplicity of small cups 3, a container of antibody solution 5, and solution containing antigen tagged with a radioactive isotope 8. The sample from one of the cups is withdrawn through pipette 9 which is on a raisable and rotatable bracket such that after a sample is extracted, the pipette is rotated upwardly and away from the cup, enabling the disc to rotate, bringing the next sequentially placed cup into alignment with the pipette 9. During the period of the rotation of the disc 1, and when samples are not being withdrawn, the pipettes 9 and 15 can be placed into container 11 which contains a buffer solution. In this manner, a space of buffer solution is ultimately provided in conduit 13 which separates adjacently moving samples. Antibody solution from source 5 and tagged antigen solution from source 8 are extracted by pipettes 15. Pick-up of the tagged solution is intermittent and pick-up of the antibody and samples can be intermittent or continuous. In other words, one can have a continuous feed of the sample and intermittent pick-up antibody, or can have continuous feed of antibody and intermittent feed of the sample. Thus, one can analyze the same sample solution with different antibodies, or one can analyze different samples with the same antibody. For example, one patient serum could be placed into 5 to 8 stationary containers and drawn coincidentally with a variety of antigen-antibody pairs placed on the rotating disc.

Suction for the operation of the pipettes 9 and 15 is provided by a vacuum created by a laminar flow type pump, such as a multichannel peristaltic pump 17. The sample and the solutions are drawn into conduits 7 and simultaneously mixed in conduit 13 for 1 to 30 seconds before being lead to incubator 19. Pick-up and mixing of a new sample solution can occur as often as once every one to three minutes.

Instead of two separate solution sources 5 and 8, a very neat package could be formed by having small cups or vials 21 placed into series on the rotatable disc 1. Thus, one cup would contain the sample and the other two of the three cup series would contain the other solutions. Thus, it might be possible to have one series of cups for measurement of insulin digoxin, another series of cups for measurement of thyroid, etc., possibly all for the same patient, wherein each series containing one cup of the same sample, which may contain a variety of antigens, or the system can be used for testing many samples from different patients in a continuous manner. Disc samplers are known and are disclosed in U.S. Pat. Nos. 3,902,371; 3,038,340; 3,424,557; 3,134,263 and 3,230,776.

Another alternative is to use a conventional fraction separator, instead of the disc sampler, to introduce the samples into the system.

After the solutions are mixed by the pumping action, the mixture is passed through conduit 13 and into an incubation chamber where the mixture will be held under standardized conditions for a fixed predetermined incubation time period.

The incubation chamber may take many forms, however, one of the most advantageous is a long coil-like conduit 23 as shown in FIG. 4 which is held at a predetermined incubation temperature. The flow rate of the sample solution through the incubation may be adjusted so that the reaction is sufficiently completed by the time the sample solution traverses the length of the conduit. A multitide of sample solutions 25 can be present in the incubation conduit at the same time, each separated by a buffer solution space 27. The buffer space 27 not only separates sample solutions, but also picks up tailings so that the next succeeding sample will not be contaminated. Since the solutions in conduit 23 are moving in laminar flow, there is, of course, a potential flow problem with the fluid in the center of the tube moving at a faster rate than at the edges. This potential problem can be quite easily dissipated by intermittently introducing bubbles in regularly spaced intervals into conduit 13, through bubbler 14, which serves to move the fluid along at a more uniform rate. This technique is disclosed in Skeggs U.S. Pat. Nos. 2,797,149 and 2,879,141.

In one such system which has now been constructed, as many as 15 samples have been under varying stages of incubation at one time.

The incubation temperature will, of course, depend upon the particular antibody-antigen system under study. In general however, the incubation temperature may vary from 0° to 60° C, and often incubation can be effected at room temperature.

The flexibility of this system is quite excellent and the system may be used for continuous assay of different systems. Thus, each sample solution extracted and introduced into conduit 13 may contain a different antigen-antibody system. It is not even necessarily required to readjust the incubator conditions in many cases, each time the antibody-antigen system is changed. It is only necessary that the calibration of the equipment for standardized samples be made under the same conditions as those used for the unknown. That is to say, it is not necessary that the incubation period be sufficient for the reaction to go to completion. It is only necessary that the incubation period for the samples be the same as the calibration. This is in sharp contrast to prior systems which in general required the reactions to go to completion for success. Of course, the closer to completion and equilibrium the system is carried during incubation, the more sensitive will be the assay. The length of incubation may vary from 1 minute to 30 minutes and even up to 1 day, depending upon the particular system. In general, if the incubation time is unacceptably long, it is possible to speed incubation by the addition of more antibody or altering the temperature.

Alternatively, the sample can be moved into one of a plurality of containers which is held under predetermined incubation conditions after which a pipette or similar device removes the incubated sample from the container and moves it toward the isolating valve 31.

At the termination of the incubation period, the sample is passed through conduit 29 as shown in FIG. 3 into an isolation valve or by-pass valve 31. The driving force for the movement of the sample through the system to this point is usually due to the pressure created by the peristaltic laminar flow pump.

The isolation of by-pass valve 31 connects the conduit 29 with conduit 33 and, alternatively, with conduit 41 to waste. Conduit 33 leads to the radioactivity detector 35. At the start of the flow system, valve 31 is opened to conduit 33 and the incubated sample is directed into the radioactivity detector 35. As the incubated sample passes through the conduit 37 within the radioactivity detector 35, the amount of radiation is measured. The radioactivity detector used herein is conventional, and any suitable detector may be used such as a NaI gamma detector. Alternatively, a liquid scintillation counter, conventionally available may be used herein. The appearance of a threshold level of radioactivity in the detector triggers a predetermined timing sequence which begins scaling the sample for a predetermined period of time, usually 1 minute. This timing means 48 is set after a comparator circuit 47 indicates that the threshold of radiation is present. Control signals from the timing means 48 thereafter sets off various valves in a sequence necessary to cause the sample solution to be brought to a separator 51, where a portion of a free antigen and free isotope tagged antigen will be separated from a portion of antigen-antibody and tagged antigen-antibody complexes. Thereafter, one of the portions will be brought into a small reservoir cup 55 in a radioactivity detector and scaled for a predetermined time period, usually about one minute.

Thus, the radioactivity detector senses the sample, can determine how much sample has been applied to the column and finally accurately and with known statistics measures the amount of bound radioactivity. It is thereafter easy to compute the ratio of radioligand bound to total radioactivity in each sample and to construct standard curves from these ratios. Alternatively, standard curves can be constructed on the basis of only the bound radioactivity if flow characteristics are sufficiently constant and stable. The timing for each sample is thus exactly the same and is not influenced by small variations in the pumping rate, which can occur over long periods of time. A small variation in the amount of sample applied to the column is thus inconsequential because the bound/total ratio, which is computed for each sample does not depend upon constant sample radioactivity.

The timing means 48 measures predetermined time sequences after which it sends out control signals through line 39 to activate the isolation valve 31, which thereby isolates the measurement portion of the system from the incubation portion of the system. The time sequence measured before valve 31 is activated, is sufficient to at least enable the entire sample to pass into the detector 35 before the measurement system is isolated. In other words, the valve 31 will usually close at some point in time as buffer solution spaces 27, which separates adjacent sample solutions 25 to be measured, is passing through the valve 31.

One very interesting aspect of this illustration is that the first radiation measurement is made as the sample is kinetically passing through the detector conduit. Usually a kinetically obtained measurement is considered to be too inaccurate for practical application. The present inventors, however, have found that the kinetic measurement is proportional to the static measurement, and can be used to compensate for losses of isotopes in the system. The kinetic measurement is also sufficiently accurate to enable its use to control the apparatus, as in the present invention. A recording means 49 is provided which is coupled to the comparator circuit 47 and the timing means 48, which is used for recording the amount of radioactivity in the kinetic and subsequently the static measurements. These measurements will be compared to calibration standards for the ultimate determination of the amount of specific antigen in the unknown sample using a computer 80 which is interfaced to the recording means 49 and timing means 48.

After the isolation valve 31 is closed, thereby diverting the feed from conduit 29 into waste conduit 41, a means can be provided for increasing the speed of the sample solution. In FIG. 3, this means takes the form of a high flow rate buffer solution inlet valve 43 which is opened simultaneously as the isolation valve 31 is closed, by predetermined signal from timer 48 from line 45. A buffer solution at high speed enters through conduit 44 into the conduit 33. The high flow rate buffer solution pushes the sample solution through conduit 50 into and through a separator column 51. This high flow rate may be needed because the resistance of the separator column might otherwise prevent the free flow of the solution therethrough. The high speed turbulent buffer solution also acts to wash any tailings from the sample solution into a separator column, so as to prevent contamination of subsequent sample solutions and to speed the appearance of the isotope solution in the radiation detector. In general, the high flow line can feed buffer at a rate of 0.5 ml/min to 50 ml/min and preferably 3 ml/min to 10 ml/min, depending, of course, upon tube and valve size.

The flow rate through the separator column 51 is controlled by the hydrostatic head created by pump 17 and the outlet of conduit 54 when the air trap valve 85 is energized to connect conduit 86 with conduit 84 which is at atmospheric pressure. As demonstrated in FIG. 5, the air trap valve 85 is deenergized simultaneously as the high flow buffer inlet valve 43 is actuated and the isolation valve 31 is closed. This causes the hydrostatic pressure to increase in the column 60 and the rate of flow through the column 60 increases as it emerges through conduit 52. The flow rate now nearly equals the flow rate of the high flow buffer line 44.

The separator column 51 serves to separate the sample solution into two portions: a first portion containing the unreacted antigen and unreacted antigen which has been tagged with the isotope, and a second portion containing the antibody-antigen complex and the antibody-tagged antigen complex. This separation can be accomplished by a variety of means, some conventional and some not conventional. In one technique preferred by the present inventors, the separator is a column which is filled with an adsorbent 60 which adsorbs any antigen which is not bound to an antibody. The column may vary from 0.1 cm to 20 cm in height and may contain between 0.1 and 100 g of adsorbent. It may be used at temperatures ranging from 0° C to 90° C.

The adsorbent may be non-particulate, such as a coating on the inner -walls of a flow column, or it may be in particulate form. When it is in particulate form, it may have a particle mesh size of from 10-1000 mesh, depending upon the hydraulics of the system. If the adsorbent is in a particulate form, the particles may be packed into the flow columns by gravity using a slurry of adsorbent particles. If desired for closer packing, pressure may be used.

In the instance of this illustration, the types of adsorbents which are used to fill the column can be any material which selectively adsorbs free antigen in solution and will not adsorb the antigen-antibody complex. Alternatively, a high concentration of immunoreactive substance, such as a specific antibody may be bound to a solid support to adsorb unreacted antigen. Examples of suitable solid support materials to be used for given separations is indicated in Table III. Coupled antibodies may be used to remove free antigens from solution and conversely when the separation being made is between the antibody-antigen complex and free antibody, coupled antigens may be used to remove the antibodies. Alternatively, coupled antibodies may be used to remove other antibodies and antibody-antigen complexes from solution leaving free antigen in solution.

For any give antigen or antibody multiplicity of separating materials are available, such as those listed in the following Table IV which may be used singly or in combination.

TABLE III

SPECIFIC EXAMPLES OF IMMUNOREACTIVE MATERIALS USABLE FOR IMMUNOASSAY SEPARATIONS

| Solid Support Material | Procedure for Coupling Antibody or Antigen | Examples of Commercially Available Material which can be used |
|---|---|---|
| Agarose | Cyanogen Bromide activation | Sepharose |
|  | Periodate activation | Biogel A |
|  | N-hydroxysuccinimide derivitization |  |
|  | Hydrazido derivitization |  |
|  | Coupling to N-hydroxysuccinimide derivatives | Affi-Gel |
|  | Carbodiimide coupling | Affi-Gel CM Biogel |
| Polyacrylamide | Carbodiimide coupling | Biogel D |
|  | Glutaraldehyde activation | Biogel CM-2 |
| Styrene divinylbenzene polymer Polystyrene | Chloromethylation | Bio-Beads S |
| Glass | P-nitro aryl and p-amino aryl derivitization | Corning controlled pore glass |
|  | Bonding to dextran | Glycophase G |
|  | Carbodiimide coupling |  |
|  | N-hydroxysuccinimide derivitization |  |
|  | Phenylhydrazine-HCl derivitization |  |
|  | Thiourea coupling |  |
|  | Glutaraldehyde activation |  |
|  | Periodate activation |  |
| Cellulose | Carbodiimide coupling | CM-cellulose |
| Acrylic polymer | Carbodiimide coupling | Bio-Rex |

TABLE IV

ANTIGENS TO BE ASSAYED AND MEANS FOR SEPARATING FREE AND ANTIBODY-BOUND FORMS

| Possible Antigens | Separation Means (Examples) |
|---|---|
| Digoxin | Absorption on charcoal |
|  | Ion exchange binding/absorption to Dowex resin |
|  | Binding to anti-digoxin antibody coupled to Agarose |
| Thyroid Stimulating Hormone (TSH) | Ionic binding to QAE-Sephadex ion exchange material |
|  | Binding to anti-TSH antibody coupled to Agarose |
| Angiotensin I | Anion exchange binding to Dowex resin at high pH |
|  | Binding to anti-Angiotensin I antibody coupled to Polyacrylamide |
| Thyroxine | Absorption to charcoal |
|  | Ion exchange binding/absorption to Dowex resin |
|  | Binding to anti-thyroxine antibody coupled to silica glass |
| Insulin | Ion exchange binding to Dowex resin at high pH |
| Cortisol | Absorption to polystyrene-divinylbenzene resin or charcoal |
| Cyclic Nucleotides | Absorption to charcoal |
|  | Ion exchange binding/absorption to Dowex resin |
|  | Binding to anti-cyclic nucleotide antibody coupled to Agarose |
| Glycoproteins (various) | Binding to Conconavalin A coupled to Agarose |

In one embodiment of the separating means, the column is packed with a region of charcoal and a region of an anion exchange resin. Usually the antigen carries a partial charge which enables it to be adsorbed onto the ion exchange resin. If radioactive impurities are present in the radioactive antigen and they are uncharged, they will not adsorb onto the ion exchange resin, but will be adsorbed onto the charcoal. Moreover, frequently there are radioactive impurities which can be adosrbed by the ion exchange resin, but not on the charcoal. Consequently, by using both materials as adsorbents, less pure reagents can be used for this radioimmunoassay process. Since the adsorbent(s) in the column is capable of adsorbing unbound antigen from a multitude of samples, the adsorbent in the column does not require frequent changing.

In another embodiment of the adsorption process in the column, it is possible to reverse the adsorption process by adsorbing the bound antigenantibody complex and allowing the free antigen to pass on through the column for measurement.

Unlike any previous process in which a separating means is reused, the present process is not regenerated between samples. The adsorbed material is not removed and adsorbed material from multiple successive samples is accumulated on the column without any appreciable degradation of its performance. Uniquely, the separation material may be immobilized antibody or any immunoreactive material or a mixture of different separation materials in combination, whether immunoreactive or not may be used in combination as noted above.

Unlike all previous "solid phase" manual and automated immunoassay processes, the binding capacity of the adsorbent material used in the present process is in a sufficient excess to remove substantially all of the desired components from solution. In fact, the capacity of the adsorbent material is such that literally hundreds of samples can be processed sequentially without loss of separation efficiency. In contrast, conventional practice of solid phase immunoassay techniques requires low enough amounts of immobilized antibody so as to bind only a fraction of the antigen.

The residual sample is eluted from separator 51 by the high flow rate buffer and passes through conduit 52 into fill valve 53 which had been opened by a predetermined signal from timing means 48. Once the entire eluted portion passes through the fill valve 53, it si again closed, thereby diverting additional buffer coming from the separation column 51 to waste through conduit 54. The column is now ready to receive the next sample. The portion being measured is thus passed into the static measurement section 55 of the radioactivity measurement detector 35 through conduit 56. The static measurement section 55 is shown in FIG. 3 as a cup having an inlet aperture 57 situated at the base thereof. The residual sample flows from the valve 53 through line 56 and into the cup 55 through lower aperture 57. After the residual sample fills the cup, a radioactivity level count for a predetermined time which is controlled by timing means 48 is made and recorded by recorder 49.

At a predetermined time during the time interval when the radiation level is being determined, timing means 48 sends a control signal to by-pass valve 31 which reconnects conduit 29 with conduit 33 and permits the next sequential sample solution to begin its ascent to the detector 35. At a predetermined time after conduit 29 is reconnected with conduit 33, the timing means 48 sends a signal and valve 59 is opened, which connects conduit 61 with conduit 63 which is connected to a vacuum source developed by the peristaltic pump pumping against valve 59 through conduit 63. The solution in the cup 55 is thereby rapidly evacuated through exit port 65 and is disposed of. The control mechanism can be set, if desired, such that at the completion of one control sequence, and hence completion of analysis of one sample, the indication level must return to a predetermined minimum base line before the mechanism can be reactivated to begin the analysis of the next sample.

In the above-discussed arrangement, the inside walls of cup 55 may be made of a non-adhering material such as teflon or polyphenylenesulfide. Moreover, the design of the cup with the inlet and outlet apertures situated at the base of the cup functions to avoid splashing so that the cup will empty quite cleanly even without the introduction of the buffer wash solution. Simultaneous with the activation of valve 59, the timing means sends a signal to stop the recording means 49 and causes the recording means to transfer the accumulated counts to computer 80 for data processing as determined by the software programs. The recording means 49 then resets and is ready to record data for the next sample.

Before the isolation valve 31 is reopened, the high flow rate buffer inlet port 44 is closed by a control signal from the timer. When the isolation valve 31 is reopened, connecting conduits 29 with 33, the pressure in conduit 33 approximates that in conduit 29 so that there is no sudden backwash through the incubation system. Similarly, when the by-pass valve 31 is in its closed position, thereby connecting conduits 29 with 41, the pressure in conduit 41 approximates that in conduit 33 since the outlets of conduit 41 and conduit 54 are physically held at the same hydrostatic pressure head. Thus, the flow rate of samples is not altered when valve 31 is energized or deenergized. A typical timing sequence for emitting control signals is shown in FIG. 5. Note that the difference in time between the shut off of the isolation valve 31 and the shut off of the high flow stream valve 43 and energizing of the column air trap valve 85 allows the conduits 33 to reach the same hydrostatic pressure as conduit 29 so that backflow or alteration in flow rate does not occur when the conduits 29 and 33 are reconnected. In addition, air space 70 about the column bed 60 is now at atmospheric pressure.

To obtain the concentration of the antigen in the original sample, the measured value is compared to a pre-obtained curve obtained by plotting a series of measured values from standard solutions having known concentrations of antigen. The standard solutions are run through the test procedure under the same incubation time and temperature conditions to which the solutions to be analyzed are subjected, and the data obtained are then plotted to form the graph of the standard curve.

The major advantage of the present method is that it provides a fully automated procedure for the measurement of antigens or antibodies in a test sample, in only a fraction of the time previously required by conventional immunoassay techniques. The present method makes it possible to run a series of tests of widely varying antigen-antibody interactions without any disruption in continuous operation of the apparatus. Consequently, the system does not require the control of a skilled operator, and even unskilled labor can be used to perform the relatively simple tasks required to set up the present system. Since there are literally hundreds of drugs, hormones and biochemically important compounds currently measured by manual application of the radioimmunoassay such as analyses of digoxin, insulin, angiotensin I, thyroxin, cyclic AMP, and the like, the present method provides a means for rapidly and accurately conducting these analyses.

This system also allows the simultaneous detection of several antigens in the same sample. In this instance, several different isotopes are used with the different antigens. The radioactivity detector will thus detect the different levels of radioactivity emitted by each of the isotopes and by computerized selectivity, simultaneous determination of two or more antigens can be made.

Having generally described the invention, a more complete understanding can be obtained by reference to certain specific examples, which are included for purposes of illustration only, and are not intended to be limiting unless otherwise specified.

Assays for digoxin, cyclic AMP, cyclic GMP, insulin, angiotensin I and thyroxine are easily performed with this process. In these cases, the sample, isotope solution and antisera were drawn for 30 seconds with a 2-½ minute wash between samples. The timing means was preset as shown in FIG. 5. Air bubbles were introduced at the rate of 0.32 ml/min into conduit 14. The conduit 63 was pumped at 3.9 ml/min to create suction to rapidly evacuate the static counting cell 55 when valve 59 was opened. Table I details the essential details of these assays with the regard to reagents and flow rates. The coefficient of variation for these assays was about 2%.

EXAMPLE 2

Figure 7:
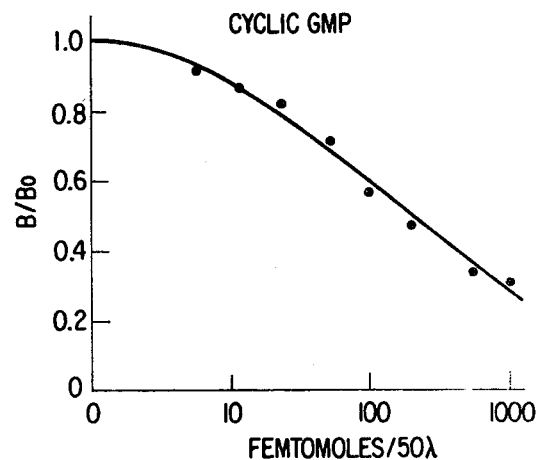
FIG. 7 is a standard curve for cyclic GMP.

FIG. 7 demonstrates a standard curve for cyclic GMP after the standards have been acetylated. It has been suggested that cyclic GMP could be an important regulator of processes controlled by the parasympathetic nervous system. In addition, some workers feel that cyclic GMP could be an important indicator of cell growth and its presence in urine could be used to detect certain organs malignancy. The sensitivity shown here is sufficient to measure cyclic GMP in less than 1 microliter of human urine.

EXAMPLE 3

Figure 8:
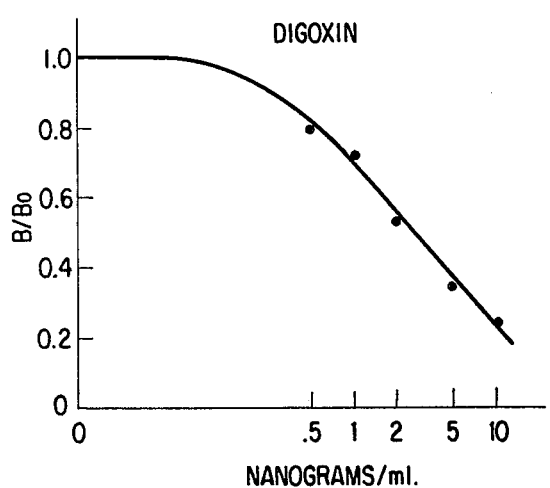
FIG. 8 is a standard curve for Digoxin.
Figure 9:
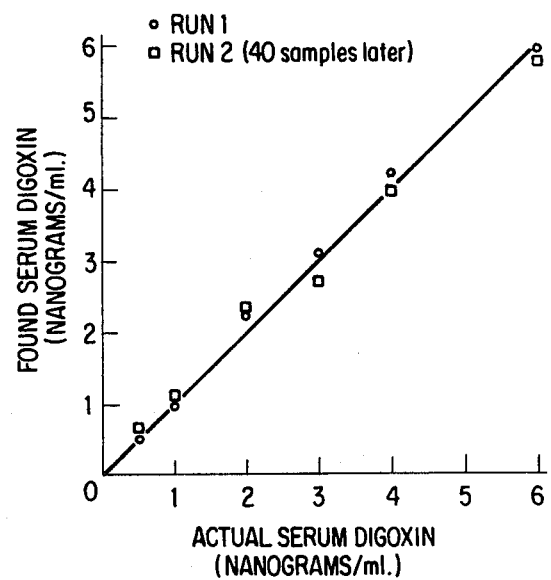
FIG. 9 is a comparison of commercial Digoxin standards with standards determined by the present invention.

FIG. 8 reveals a standard curve fr digoxin. It takes less than 4 minutes to do a single determination. Digoxin is an important cardiac glycoside taken by between 3–5 million people in the USA alone. The drug markedly stimulates the heart in people with congestive heart failure. However, the drug is also very toxic to the heart causing rhythm disorders. Serum digoxin levels of 1.4 Ng/ml are considered therapeutic while toxic levels are considered when the serum level rises about about 2.5–3 Ng/ml. As can be seen, the assay method has sufficient sensitivity to make this distinction. When commercial serum digoxin standards were repetitively assayed, as excellent correlation was found as shown in FIG. 9. In addition, this Figure demonstrates the excel-

TABLE I
REAGENTS FOR THE AUTOMATED RADIOIMMUNOASSAY

| Flow Rate→ | 0.1 ml/min | 0.1 ml/min | 0.1 ml/min | | 0.23 ml/min | 7.8 ml/min | | | |
|---|---|---|---|---|---|---|---|---|---|
| | | | | | Buffer Solutions | | | Time | |
| | Compound (Sample | $^{125}$I-Radioligand (0.2 μCi/ml 8 | Antisera | Separation Column 60 | Buffer Line 30 | High Flow 44 | Collected for B$_o$ | Delay Coil (min) | Temp. |
| | Digoxin | Digoxigenin 3-O-Tyrosine | 1:30,000 | AG 1-X8 100–200 mesh plus charcoal 60–200 mesh | Solution 1 plus 5 mg/ml bovine serum albumin | Solution 1 without Brij-35 | 3390 | 3 | Ambient |
| | Cyclic AMP | ScAMP-TME | 1:2000 | | | | 3325 | 21 | Ambient |
| | Cyclic GMP | ScGMP-TME | 1:1000 | | | | 2153 | 21 | Ambient |
| | Insulin | Monoiodinated Insulin | 2000 tube commercial antisera in 100 ml | or AG 1-X8 100–200 mesh 9 × 45 mm | Solution 2 | Solution 2 without Brij-35 | 1990 | 21 | 39° C |
| | Angiotensin I | Monoiodinated Angiotensin I | 1:2500 | | | | 2290 | 21 | Ambient |
| | Thyroxin (T-4) | Thyroxin | 500 tube commercial antisera in 50 ml | | | | 1540 | 9 | Ambient |

Solution 1 is 50 mM sodium acetate, pH 4.7 containing 0.015% Brij-35. Solution 2 is 50 mM Tris-HCl, pH 9.2 containing 0.015% Brij-35. Thyroxin isotope solution also contained 1:5000 Sodium Merthiolate. Radioligand was dissolved in the Sampler Wash buffer. Antisera were diluted in the Buffer line buffer. ScAMP-TME (2'-O-Succinyl-Cyclic AMP Tyrosire Methyl Ester) and ScGMP-TME (2'-O-Succinyl-Cyclic GMP Tyrosine Methyl Ester) were labeled with [$^{125}$I]. Specific activity was between 100–200 Ci/mmole. [$^{125}$I]-Digoxigenin-3-O-Tyrosine (Sp.act. 1500Ci/mmole) Monoiodinated Insulin (100 μCi/μg), monoiodinated Angiotensin I (687 μCi/μg), Thyroxine[$^{125}$I] (118 μCi/μg) diluted in either solution 1 or 2.

EXAMPLE 1

Figure 6:
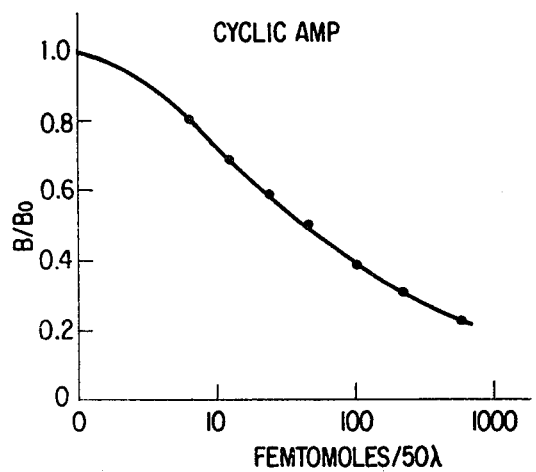
FIG. 6 is a standard curve for cyclic AMP.

FIG. 6 shows a standard curve for cyclic AMP after the standards had been acetylated (500 μl standard + 10 μl triethylamine + 5 μl acetic anhydride). This data and all following data for standard curves is plotted with the concentration of ligand being measured on the abscissa (log) vs the ratio of radioactivity found for standards to that when only the radioligand was present and is presented as the B/B$_o$ ratio. Whether or not the results are normalized by correction using the first count (count 1) the end result is the same, since the first counts would be the same if perfect pumping reproducibility occurred. This compound is though to be an important mediator of hormone action.

lent instrument stability over a long period of time.

EXAMPLE 4

Figure 10:
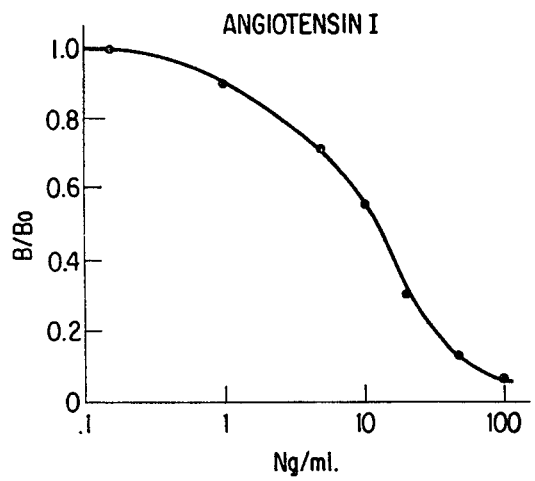
FIG. 10 is an Angiotensin I standard curve.

FIG. 10 illustrates a standard curve for Angiotensin I. While plasma levels are very low, the radioimmunoassay for Angiotensin I is very useful to measure plasma renin activity (PRA). Normal PRA is about 1–6 Ng/ml Angiotensin I/hour and abnormal from 10–100 Ng/ml Antiotensin I/hour. It can be seen that the method can easily make this distinction.

EXAMPLE 5

Figure 11:
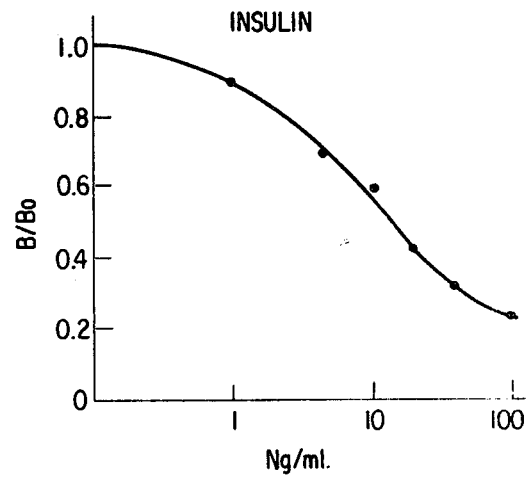
FIG. 11 is an insulin standard curve.

Insulin is an important hormone in glucose homeostasis. Measurement of serum or plasma insulin can be of aid in the diagnosis and mangement of patients with diabetes. The assay of insulin normally takes several days using conventional techniques. FIG. 11 demonstrates a standard curve for insulin. The total assay time for an individual insulin sample in the present system is only 21 minutes. This could be useful in cases where it is critical to know the serum insulin concentration in order to develop a therapeutic plan for a diabetic patient in insulin imbalance. The sensitivity of this assay is sufficient to monitor insulin in the concentrations normally encountered in clinical medicine.

EXAMPLE 6

Figure 12:
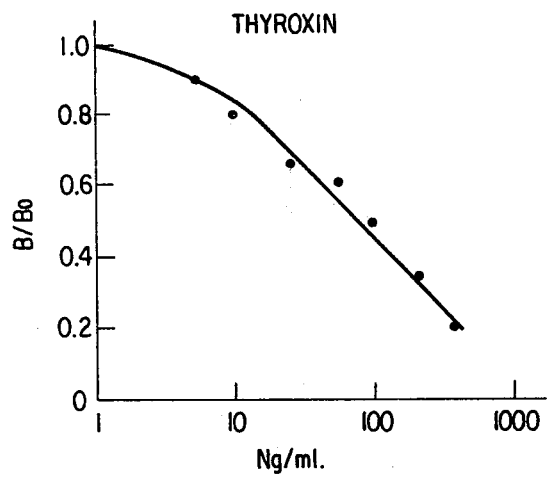
FIG. 12 is a thyroxine standard curve

FIG. 12 demonstrates a standard curve for thyroxin. The sensitivity of the automated assay is comparable to other radioimmunoassays for thyroxine.

EXAMPLE 7

The automated radioimmunoassay system of the present invention is especially versatile being able to alternately sequentially assay for different substances. The following nine substances at the concentrations indicated were placed in the sampler tray and their respective isotope solutions were drawn as each sample was processed. Incubation was for 21 minutes at 39° C. No delay between samples occurred and it took 27 minutes for all nine samples to be drawn into the instrument. Notice the excellent reproducability and the ability to switch between different antigens without any equilibration time needed.

TABLE II

| Sample No. | Compound | Ng/ml | B/B$_o$ |
|---|---|---|---|
| 1 | Angiotensin I | 0 | 1.00 |
| 2 | Angiotensin I | 25 | 0.23 |
| 3 | Insulin | 0 | 1.00 |
| 4 | Thyroxin | 0 | 1.00 |
| 5 | Insulin | 25 | 0.45 |
| 6 | Thyroxin | 0 | 1.05 |
| 7 | Insulin | 25 | 0.42 |
| 8 | Angiotensin I | 25 | 0.20 |
| 9 | Insulin | 0 | 0.95 |

EXAMPLE 8

Figure 13:
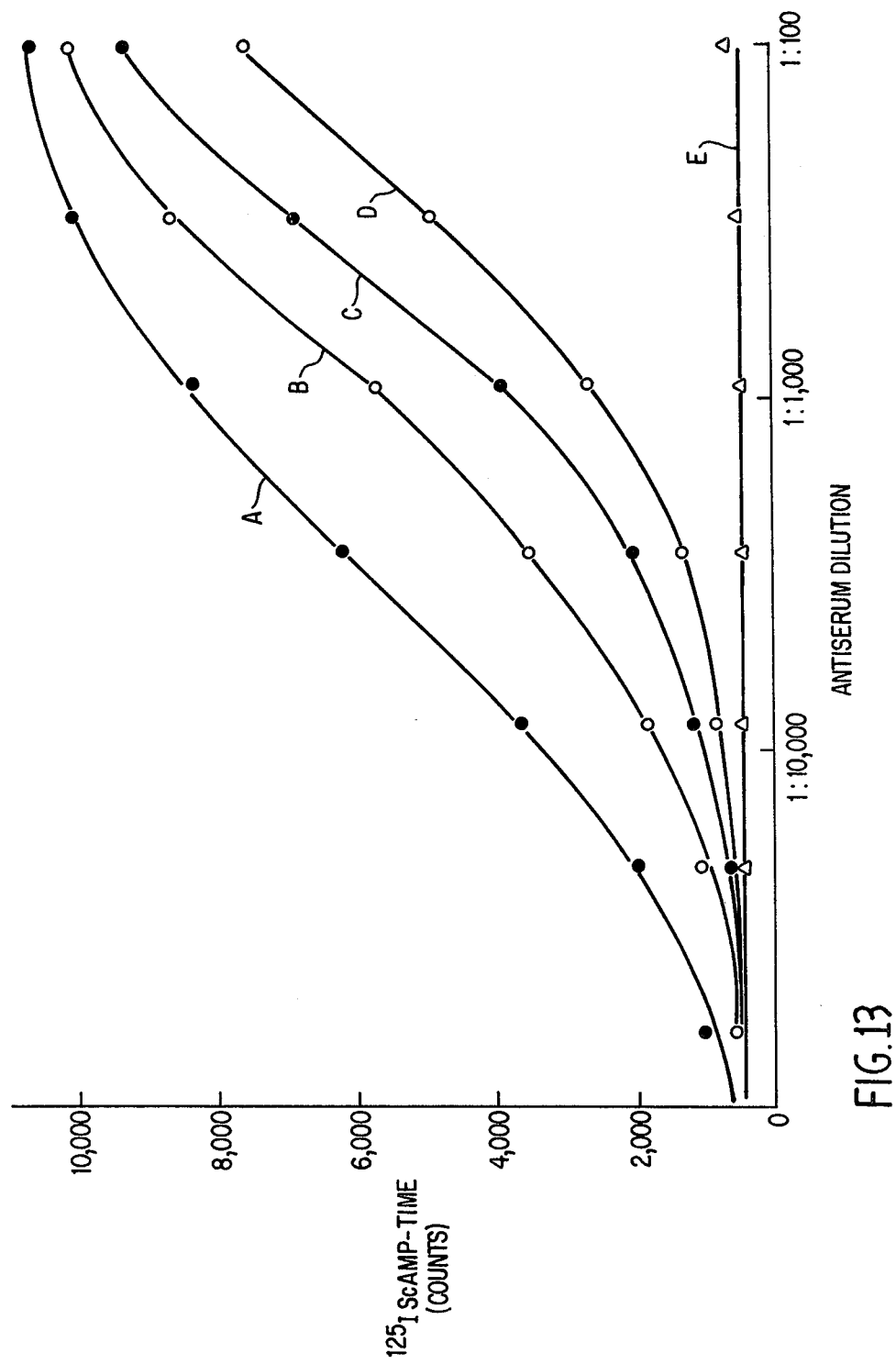
FIG. 13 is a measurement of anti-cyclic AMP antibodies.

FIG. 13 demonstrates the measurement of anti-cyclic AMP antibodies in goat sera harvested from goats immunized with cyclic AMP chemically coupled to human serum albumin. The present automated immunoassay system was used to assay for anti-cyclic AMP antibodies using $^{125}$I-labelled succinyl cyclic AMP tyrosine methyl ester. Curve A is the dilution curve of antiserum bled from a goat 17 days after a booster immunization. B is the curve of antiserum bled 37 days after the same boost. Similarly, curves C and D represent anti-cyclic AMP antibodying binding in antisera obtained from a second goat bled 17(C) and 37(D) days after boosting. E represents control serum obtained from an un-immunized goat.

EXAMPLE 9

Figure 14:
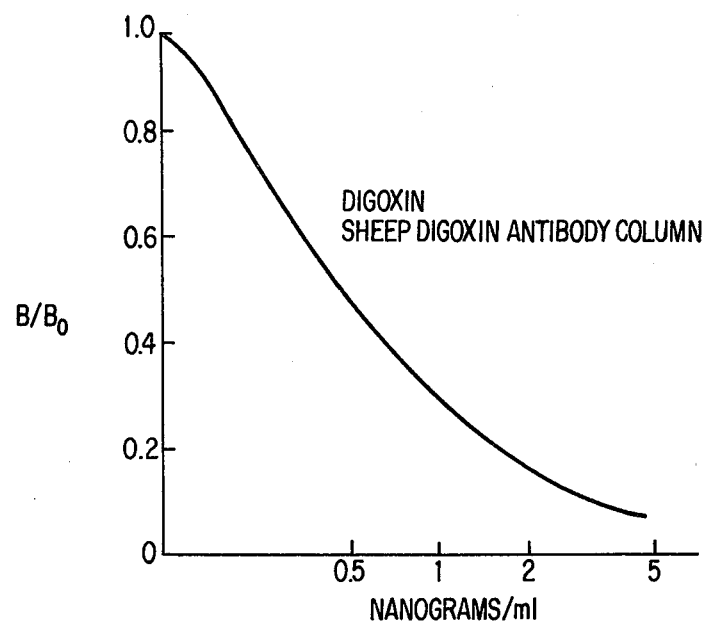
FIG. 14 is a standard curve for Digoxin using anti-digoxin separating column.
Figure 15:
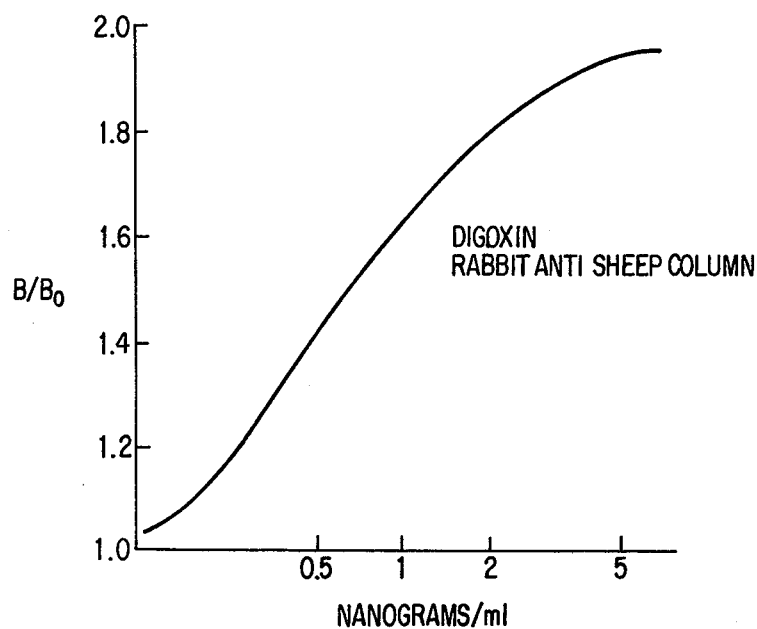
FIG. 15 is a standard curve for Digoxin using a rabbit, anti-sheep IgG column.

FIG. 14 demonstrates an immunoassay technique for digoxin wherein the standard curve is obtained using a separation means wherein antisera to digoxin (raised in sheep) is covalently linked to 50-100 mesh agarose beads.

EXAMPLE 10

FIG. 5 demonstrates an immunoassay technique for digoxin. The initial incubation utilizes sheep anti-digoxin serum. Separation is achieved on a column containing immobilized rapid anti-sheep IgG.

What is claimed as new and desired to be secured by letters patent of the United States is:

1. In a method for effecting immunoassay of a multiplicity of samples, each possibly containing an antigen or an antibody to be assayed, wherein each sample is incubated with a solution containing a detectable antigen or antibody to form a multiplicity of mixtures, each mixture containing as components:complexed antigen-antibody, non-complexed antigen and non-complexed antibody, separating at least one of the components of said mixture by adsorption and thereafter detecting the quantity of detectable antigen or antibody, in the non-adsorbed portions of the mixture, the improvement which comprises continuously and sequentially separating at least one component intended to be separated from each of said multiplicity of mixtures by passing a first mixture from said multiplicity of mixtures over an adsorbent which adsorbs the components intended to be separated from said mixture, removing from said adsorbent the non-adsorbed portion of said mixture, and repetitively passing each next succeeding mixture from said multiplicity of mixtures over the same adsorbent without intermittent removal of the components of the mixture which had been adsorbed onto said adsorbent from the preceding mixtures, and removing from said adsorbent the non-adsorbed portion following each pass, wherein each sequential mixture is in contact with said adsorbent for a residence time which is sufficient to permit adsorption of the said component, but which is insufficient to effect significant disassociation of the prior adsorbed component, and which is insufficient to effect adsorption of additional components of said mixture onto the additional adsorption sites created on said adsorbent by the prior adsorption of the components from the preceding mixture.

2. The method of claim 1, wherein the incubation of a said mixture is carried out to a point less than equilibrium such that the incubated mixture contains substantial amounts of complexed antigen-antibody, non-complexed antigen and non-complexed antibody.

3. The method of claim 1, wherein each of said samples applied to the adsorbent has of a volume of 10µl to 10ml per 100µl to 100ml of adsorbent and wherein residence time is from 1 second to 120 seconds at a temperature of from 0°-90° C.

4. The method of claim 1, wherein the said adsorbent is capable of adsorbing antigens from a mixture of non-complexed antigens, non-complexed antibody and antigen-antibody complex.

5. The method according to claim 1, wherein the adsorbent is an ion exchange resin.

6. The method according to claim 1, wherein the adsorbent is an excess of immobilized antibody which is capable of adsorbing non-complexed antigen.

7. The method according to claim 1, wherein the adsorbent is immobilized antibody which is capable of adsorbing antibody or antigen-antibody complex.

8. The method acording to claim 1, wherein the adsorbent is a combination of two or more adsorbent materials.

9. In an apparatus for effecting immunoassay of a multiplicity of samples, each possibly containing an antigen or an antibody to be assayed, which contains means for incubation of each sample solution containing a detectable antigen or antibody to form a multiplicity of incubated mixtures, each mixture containing as components:complexed antigen-antibody, non-complexed antigen and non-complexed antibody, means for separating at least one of the components of each of said mixtures by adsorption, means for detecting the quantity of detectable antigen or antibody, in one of the non-adsorbed portions of each mixture, the improvement which comprises separating means for continuously and sequentially separating at least one component intended to be separated from each of said multiplicity of mixtures which means for passing a first mixture from said multiplicity of mixtures over an adsorbent which adsorbs the components intended to be separated from said mixture, adsorbent which is capable of adsorption of specific components within the mixture contacted therewith, means for removing from said adsorbent the non-adsorbed portion of said mixture, and means for repetitively passing each next succeeding mixture from said multiplicity of mixtures over the same adsorbent without intermittent removal of the components of the mixture which had been adsorbed onto said adsorbent from the preceding mixtures, and means for removing from said adsorbent the non-adsorbed portion following each pass.

10. The apparatus of claim 9, wherein said adsorbent is in particulate form and is contained in an adsorption column.

11. The apparatus of claim 9, wherein the said adsorbent is an ion-exchange resin.

12. The apparatus according to claim 9, wherein the adsorbent is an excess of immobilized antibody which is capable of adsorbing non-complexed antigen.

13. The apparatus according to claim 9, wherein the adsorbent is immobilized antibody which is capable of adsorbing antibody or antigen-antibody complex.

14. The apparatus according to claim 9, wherein the adsorbent is a combination of two or more adsorbent materials.

* * * * *

UNITED STATES PATENT AND TRADEMARK OFFICE
CERTIFICATE OF CORRECTION

PATENT NO. : 4,104,026

DATED : August 1, 1978

INVENTOR(S) : Gary Brooker et al

It is certified that error appears in the above-identified patent and that said Letters Patent are hereby corrected as shown below:

Column 20, line 2, delete "rapid", and insert --rabbit--.

Column 21, line 16, delete "which", and insert --via--.

Signed and Sealed this

Nineteenth Day of June 1979

[SEAL]

Attest:

RUTH C. MASON  
Attesting Officer

DONALD W. BANNER  
Commissioner of Patents and Trademarks